(12) United States Patent
Hall

(10) Patent No.: US 6,364,878 B1
(45) Date of Patent: Apr. 2, 2002

(54) PERCUTANEOUS TRANSLUMINAL ABLATION CATHETER MANIPULATION TOOL

(75) Inventor: Jeffrey A. Hall, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/348,776

(22) Filed: Jul. 7, 1999

(51) Int. Cl.⁷ ............................................. A61B 18/18
(52) U.S. Cl. ........................ 606/41; 607/150; 607/122
(58) Field of Search ................. 607/115–131, 149–150; 606/41–42, 45, 48–50, 1, 207; 604/523

(56) References Cited

U.S. PATENT DOCUMENTS

| | | | |
|---|---|---|---|
| 4,306,547 A | * | 12/1981 | Lowell |
| 4,694,826 A | * | 9/1987 | Chester |
| 5,184,803 A | * | 2/1993 | Stone |
| 5,314,464 A | | 5/1994 | KenKnight et al. |
| 5,476,495 A | | 12/1995 | Kordis et al. |
| 5,591,203 A | * | 1/1997 | Fahy .......................... 606/207 |
| 5,613,937 A | | 3/1997 | Garrison et al. |
| 5,626,136 A | | 5/1997 | Webster |
| 5,636,634 A | | 6/1997 | Kordis et al. |
| 5,645,519 A | * | 7/1997 | Lee et al. .................... 600/114 |
| 5,651,761 A | * | 7/1997 | Upsher ....................... 600/114 |
| 5,674,197 A | | 10/1997 | van Muiden et al. |
| 5,697,927 A | | 12/1997 | Imran et al. |
| 5,720,719 A | | 2/1998 | Edwards et al. |
| 5,746,462 A | * | 5/1998 | Lee et al. ................... 294/64.1 |
| 5,746,763 A | * | 5/1998 | Benderev et al. ............ 606/193 |
| 5,776,187 A | | 7/1998 | Krueger et al. |
| 5,814,101 A | | 9/1998 | Wallnner et al. |
| 5,836,947 A | | 11/1998 | Fleischman et al. |
| 5,840,013 A | * | 11/1998 | Lee et al. .................... 600/114 |
| 5,848,986 A | | 12/1998 | Lundquist et al. |

OTHER PUBLICATIONS

Calkins, H., et al., "A New System for Catheter Ablation of Atrial Fibrillation", *American Journal of Cardiology*, vol. 83 (5B), 227D–236D, (Mar. 11, 1999).

* cited by examiner

*Primary Examiner*—Michael Peffley
*Assistant Examiner*—Roy Gibson
(74) *Attorney, Agent, or Firm*—Schwegman, Lundberg, Woessner & Kluth, P.A.

(57) ABSTRACT

The present tool and methods embody a percutaneous transluminal ablation (PTA) catheter manipulation tool for holding and positioning a PTA catheter, comprising a handle portion and a PTA catheter support structure. The PTA catheter is securely held in the PTA catheter support structure and the user holds the handle portion to position the PTA catheter against the treatment site. In one embodiment, the tool is made from a rigid material. In another embodiment, the PTA catheter support structure and/or the handle portion are made from a malleable material to facilitate forming to a desired shape. After treating one site, the tool may then be bent to a new desired configuration to treat the same or additional sites. In another embodiment, the PTA catheter manipulation tool incorporates, either internally or externally, a fluid delivery system that provides fluid to cool the PTA catheter support structure and/or the treatment site. In another embodiment, the support structure is pivotally mounted such that when pressed against the treatment site, the support structure will automatically position itself flush with the surface being treated.

41 Claims, 14 Drawing Sheets

PERCUTANEOUS TRANSLUMINAL ABLATION CATHETER MANIPULATION TOOL

TECHNICAL FIELD

The present description generally relates to medical tools and methods, and more particularly, a percutaneous transluminal ablation catheter holding tool and method of use.

BACKGROUND

Percutaneous transluminal ablation (PTA) catheters for tissue ablation are available for the treatment of many conditions of the heart, including atrial fibrillation, atrial and ventricular arrhythmias or dysfunction, as well as others. The PTA catheters are long, slender, and flexible such that they can be inserted through a small incision through the skin into a blood vessel, such as an artery or vein, and advanced to the treatment site near to or inside the heart. Once positioned, the PTA catheter is used to selectively ablate or "burn" selected tissue which results in a change in the physiology of the treatment site. Such treatments may be used to block electrical conduction to correct abnormal cardiac rhythm that interferes with proper organ function.

Since its initial description in 1982, catheter ablation has evolved from a highly experimental technique to its present role as first-line therapy for most supraventricular arrhythmias, including atrioventricular nodal reentrant tachycardia, Wolff-Parkinson-White syndrome, focal atrial tachycardia, and atrial flutter. Over the past five years, increasing attention has been focused on the development of catheter ablation techniques and ablation systems to cure atrial fibrillation. J. F. Swartz, et al., is credited with being the first to demonstrate that chronic atrial fibrillation can be cured using catheter ablation techniques (Swartz J F, Perrersels G, Silvers J, Patten L, Cervantez D., A Catheter Based Curative Approach to Atrial Fibrillation in Humans, Circulation. 1994; 90 (suppl 1): 1–335). These authors reported that creation of linear lesions in the right and left atrium results in a progressive increase in the organization of atrial activity until sinus rhythm is restored. M. Haissaguerre, et al., reported successful ablation of atrial fibrillation in a patient with paroxysmal atrial fibrillation by the creation of three linear lesions in the right atrium, two longitudinal and one transverse, that connected the two longitudinal lesions using a specially designed catheter (Haissaguerre M, Gencel L, Fischer B, Metayer P L, Poquet F, Marcus F l, Clementy J., Successful Catheter Ablation of Atrial Fibrillation, J Cardiovasc Electrophysiol 1994;5:1045–1052).

Currently available ablation systems are limited because they can only create singular spot lesions or short drag lesions, requiring a significant amount of time to perform biatrial lesions. Systems that can create linear lesions are currently undergoing investigation at this time and hold exciting promise for the future. One such system currently under clinical investigation is the Guidant's Heart Rhythm Technology's (HRT; Guidant Corporation, Cardiac Rhythm Management Group, St. Paul, Minn.) Linear Phased Radio Frequency Ablation System consisting of a 7 Fr., 5-mm tipped quadripolar deflectable electrode catheter and multiple pre-shaped steerable linear catheters which incorporate 12-3-mm platinum band electrodes with an inter-electrode spacing of 4 mm. Thermocouples are positioned on the outside curvature of the catheter to allow for temperature monitoring during radio frequency (RF) delivery. A variety of 3-dimensional catheter shapes, are designed to be used in conjunction with sheaths to achieve specific linear lesions within the right and left atria. The pre-shaped steerable linear catheters are created by means of a pre-shaped Nitinol stylet embedded within the shaft. These catheters are used in conjunction with the Guidant HRT Linear Phased RF Ablation Generator, which is a multi-channel RF generator capable of delivering phased RF energy at a frequency of 540 kHz to selected electrodes, in order to modify the lesion length, from localized, spot lesions to lesions which are 8 cm in length. When using the multi-electrode catheters, by delivering RF energy at adjacent electrodes out of phase with each other, a voltage gradient is created between electrodes and also to the back plate. This results in current paths both between electrodes and also to the return electrode (back plate), thereby creating a continuous linear lesion. The generator has the ability to continuously monitor the impedance and temperature of each active band electrode. Power output for pre-shaped linear catheters can be varined from 0 to 20 Watts per electrode. Power delivery is in the form of a duty cycle with a constant output amplifier with power variability controlled by varying the amount of time energy is delivered. This approach to power delivery allows for electrode cooling during the off cycle. Adjustments in the power output can be made to all electrodes at once or in three zones of four electrodes each. The generator incorporates additional safety features if excessive temperature or impedance is detected. The generator automatically shuts down power delivery to any band electrode if the impedance of that circuit exceeds a pre-set limit, or if the temperature exceeds a preset value. For the 5-mm tip ablation catheter, the RF generator will deliver RF energy with a maximal power output of 50 Watts to the tip only, while continuously monitoring the impedance and temperature of the tip electrode. Ablation duration can be adjusted from 5 seconds to 5 minutes.

Successful ablation therapy is defined as a return to normal sinus rhythm. To achieve this, lesions need to be continuous, transmural, and connected with other lesions or anatomical structures that cause blockage of atrial conduction. The seven recommended lesions are as follows: 1) right atrial isthmus ablation: linear lesion applied to the right atrium between the tricuspid annulus and the eustachian ridge, 2) right atrial inter-caval ablation: linear lesion applied along the posterior wall of the right atrium, between the superior vena cava and the inferior vena cava, 3) right pulmonary vein ablation (RPV): linear lesion applied to the left atrium, beginning below Bachmann's bundle, across the right superior pulmonary vein (RSPV) to the right inferior pulmonary vein (RIPV) and adjoining the mitral annulus, 4) left pulmonary vein ablation (LPV): linear lesion applied to the left atrium, beginning below Bachmann's bundle, across the left superior pulmonary vein (LSPV) to the left inferior pulmonary vein (LIPV) and reaching the mitral annulus, 5) superior pulmonary vein ablation (SPV): linear lesion applied to the left atrium, across the right superior pulmonary vein to the left superior pulmonary vein, 6) left atrial roof ablation (ROOF): linear lesion applied from the trigone, across the roof of the left atrium, to the left superior pulmonary vein, and 7) left atrial septal ablation (SEP): linear lesion applied to the foramen ovale to the right superior pulmonary vein. During creation of the right atrial inter-caval line, pacing is performed from each pair of electrodes at high output to assure the absence of diaphragmatic stimulation.

PTA catheters use any of a number of methods to deliver ablative energy to the tissue. Some of these methods include electric heating, microwave radiation, ultrasound radiation, and cryogenics. The energy delivery component of the PTA catheter, sometimes referred to as an electrode, is located either at the distal tip or along a portion of the distal end of the PTA catheter. When the PTA catheter is advanced through the blood vessel to the treatment site, either the tip or the side of the PTA catheter, depending on electrode type, is pressed against the tissue to be ablated.

There is a need to have the capability to apply ablation therapy non-transluminally, such as during open heart surgery, on either epicardium or endocardium. For example, some patients having surgery for the treatment of atrioventricular valve disease would benefit from ablation therapy in order to correct cardiac arrhythmias of the atria or ventricle. Up to 40% of patients requiring mitral valve replacement have concurrent atrial fibrillation (fast atrial arrhythmia) which can be treated by creation of long linear ablation lines in the atria. Since PTA catheters are currently available, there is a need to use PTA catheters non-transluminally.

SUMMARY

In general, the present tool and methods embody a percutaneous transluminal ablation (PTA) catheter manipulation tool for holding and positioning a PTA catheter, comprising a handle portion and a PTA catheter support structure. The PTA catheter is securely held in the PTA catheter support structure and the user holds the handle portion to position the PTA catheter against the treatment site. In one embodiment, the tool is made from a rigid material. In another embodiment, the PTA catheter support structure and/or the handle portion are made from a malleable material to facilitate forming to a desired shape. After treating one site, the tool may then be bent to a new desired configuration to treat the same or additional sites. In another embodiment, the PTA catheter manipulation tool incorporates, either internally or externally, a fluid delivery system that provides fluid to cool the PTA catheter support structure and/or the treatment site. In another embodiment, the support structure is pivotally mounted such that when pressed against the treatment site, the support structure will automatically position itself flush with the surface being treated.

This summary is a brief overview of some embodiments of the tool and methods of using a PTA catheter manipulation tool for holding and positioning a PTA catheter and is not intended to be exclusive or limiting and the scope of the invention is provided by the attached claims and their equivalents.

DETAILED DESCRIPTION

Figure 1:
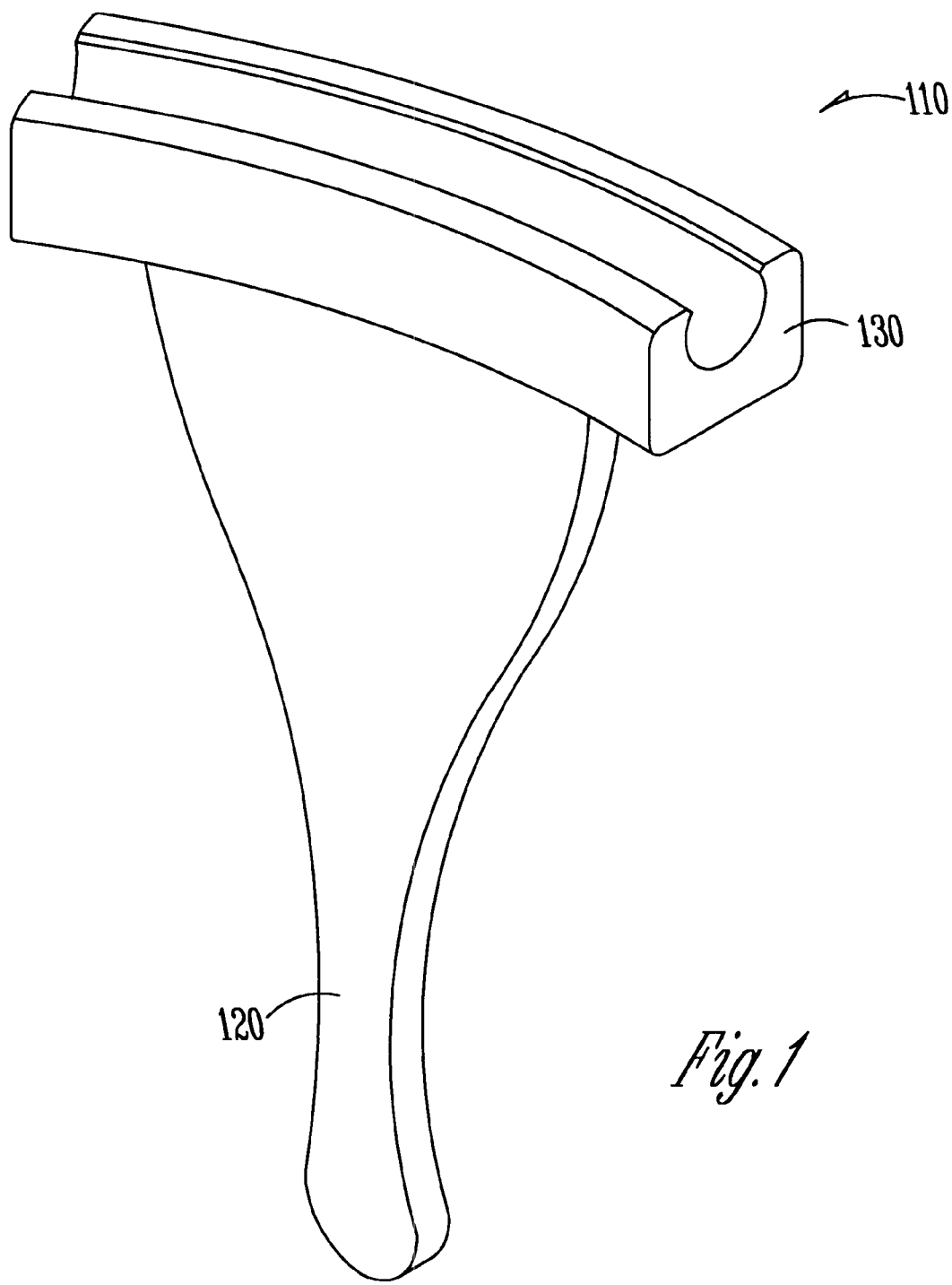
FIG. 1 is a perspective view of one embodiment of an ablation PTA catheter manipulation tool.

In the following detailed description, reference is made to the accompanying drawings, which are not necessarily to scale, which form a part hereof, and in which is shown by way of illustrating specific embodiments in which the device may be practiced. These embodiments are described in sufficient detail to enable those skilled in the art to practice the device, and it is to be understood that the embodiments may be combined, or that other embodiments may be utilized and that structural changes may be made without departing from the spirit and scope. The following detailed description is, therefore, not to be taken in a limiting sense, and the scope is defined by the appended claims and their equivalents. In the drawings, like numerals describe substantially similar components throughout the several views.

The present apparatus and methods will be described in applications involving biomedical applications. However, it is understood that the present apparatus and methods may be employed in other environments and uses.

FIG. 1 is a perspective view of an embodiment of a PTA catheter manipulation tool 110 illustrating generally, by way of example, but not by way of limitation, one embodiment of a PTA catheter manipulation tool. More in particular, the tool 110 comprises a PTA catheter support structure 130 and a handle portion 120. The PTA catheter support structure 130 is shaped to accept a PTA catheter. In the embodiment shown, the support structure 130 is in the form of a concave channel. Generally, support structure 130 comprises an elongated shape since PTA catheters are usually elongated in shape.

In one embodiment, PTA catheter support structure 130 is a relatively stiff member that is manufactured into a desired shape. The desired shape is dependent on its use such that the PTA catheter is held to create the desired lesion shape and that the handle portion facilitates access to the treatment site. In another embodiment, PTA catheter support structure 130 and/or handle portion 120 are made from a relatively malleable material or have malleable properties to facilitate bending into a desired shape, such as a curve or straight position, and retain that shape during use. In some embodiments, the malleability feature of support structure 130 and/or handle portion 120 is a property of the material that it is made. In other embodiments, the malleability feature of support structure 130 and/or handle portion 120 is facilitated by imbedding a spine of malleable material (such as a wire, rod or sheet) into flexible material that makes up the bulk of support structure 130. In another embodiment, the support structure 130 may consist of a material that can be trimmed, such as with a scalpel or scissors, to a desired length.

The handle portion 120 is of any shape that would facilitate the grasping and using the tool 110. The handle portion 120 and the PTA catheter support structure 130 may be one integral unit. In another embodiment, the handle portion 120 is detachable from the support structure 130.

Figure 2:
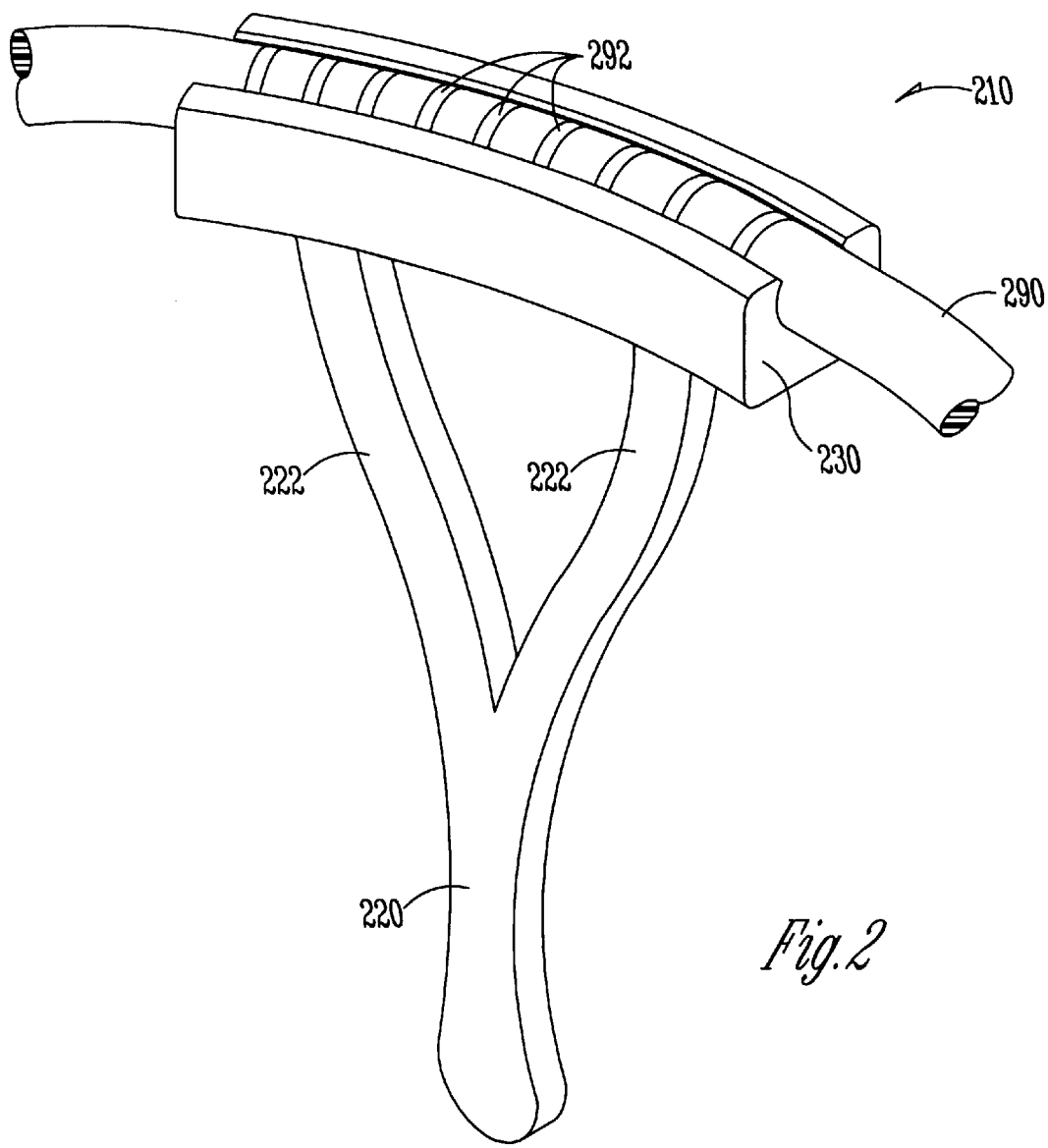
FIG. 2 is a perspective view of one embodiment of an ablation PTA catheter manipulation tool with PTA catheter attached.

FIG. 2 is a perspective view of an embodiment of a PTA catheter manipulation tool 210 illustrating generally, by way of example, but not by way of limitation, one embodiment of a PTA catheter manipulation tool having a PTA catheter attached. More in particular, FIG. 2 shows an embodiment of the tool 210 consisting of a handle portion 220, two shafts 222 and a PTA catheter support structure 230. A PTA catheter 290 is shown mounted to support structure 230 in such a way that the PTA catheter electrodes 292 are held within the support structure 230. In use, the user would hold the tool 210 by grasping the handle portion 220 and pressing the PTA catheter 290 against the treatment site.

The handle portion 220 is of any shape that would facilitate the holding and using the tool 210. In some embodiments, the handle portion 220 is connected to the PTA catheter support structure 230 with more than one shaft 222. The handle portion 220, the one or more shafts 222, and the support structure 230 may be formed as a single unit, or one or more of the entities may be detachable.

In embodiments where the support structure 230 and/or the one or more shafts 222 are made from rigid material, one shaft 222 may be sufficient to effectively transmit force applied on the handle portion 220 to the support structure 230. The one or more shafts 222 and/or the support structure 230 may be of a material that is relatively malleable to facilitate bending the tool 210 to a desired shape. If the support structure 230 and/or the one or more shafts 222 are made from a relatively flexible or malleable material, more shafts 222 may be needed to uniformly transfer force from the handle portion 220 to the support structure 230. The one or more shafts 222 may be made from a shape memory material that, upon the application of heat, such as with autoclaving, the one or more shafts 222 return to their manufactured shape. This would facilitate the reuse of tool 210. The detachability of the one or more shafts 222 from the support structure 230 allows for disposal of the support structure 230, or separate processing, such as sterilization.

The PTA catheter support structure 230 is shaped to accept a PTA catheter 290. In the embodiment shown in FIG. 2, the support structure 230 is in the form of an elongated concave channel. Depending on the type of PTA catheter used, the support structure 230 may need to possess thermal, electrical, or both thermal and electrical insulating properties.

In one embodiment, the support structure 230 is pivotally mounted to the one or more shafts 222 which allows the support structure 230 to self align when pressed against the treatment site.

Figure 3A:
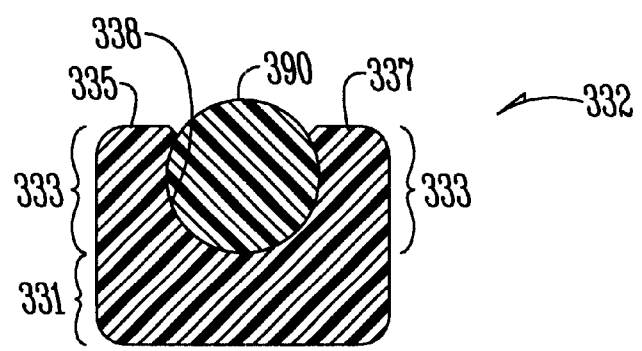
FIG. 3A is a cross-sectional view of one embodiment of an PTA catheter manipulation tool PTA catheter support structure with PTA catheter attached.
Figure 3B:
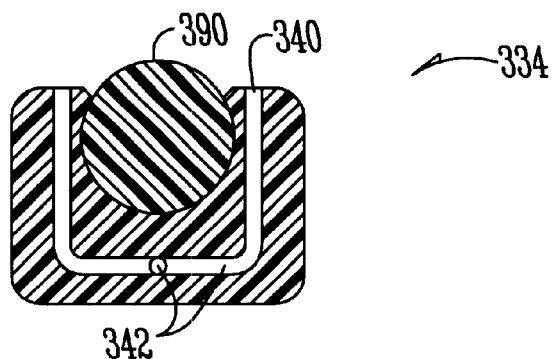
FIG. 3B is a cross-sectional view of one embodiment of a PTA catheter manipulation tool PTA catheter support structure with cooling capability, with PTA catheter attached.
Figure 3C:
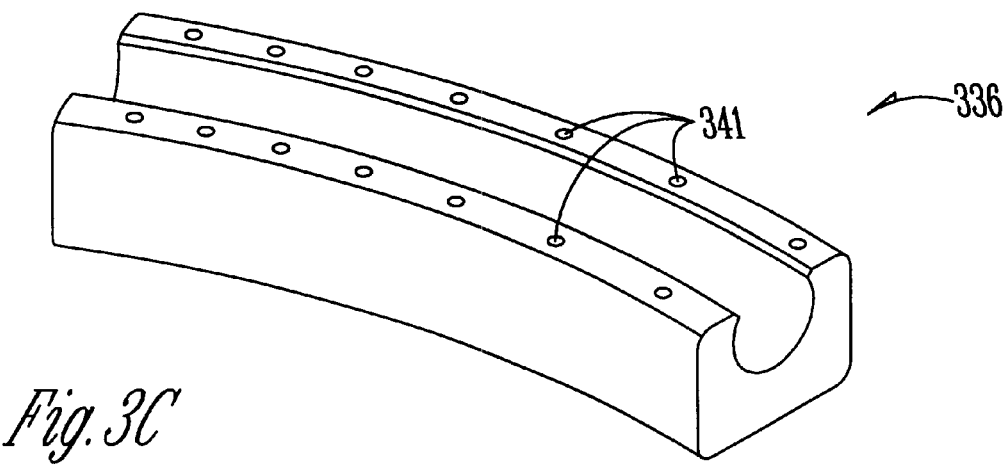
FIG. 3C is a perspective view of one embodiment of a PTA catheter manipulation tool PTA catheter support structure with cooling capability.

FIGS. 3A–C are views, illustrating generally, by way of example, but not by way of limitation, of embodiments of portions of the PTA catheter support structure. These embodiments may also incorporate fluid channels and orifices to allow cooling of the treatment site. More in particular, FIG. 3A shows a cross-sectional view of a support structure 332. The PTA catheter support structure 332 comprises a concave channel having a base 331, spaced lips 333 extending from one side of the base 331 forming a cavity 338, each lip having a free end, 335 and 337 respectively. In one embodiment, cavity 338 has a substantially circular cross section substantially conforming to and engaging a major portion of the outer surface of the PTA catheter 390. The lips 333, extending from the base 331, partially overlap the PTA catheter 390 in order to retain the PTA catheter 390 with in the cavity 338. A portion of the PTA catheter 390, when placed within the cavity 338, is exposed beyond the lips 333. In one embodiment, the support structure 332 is made from a relatively rigid material and the PTA catheter 390 is slidably inserted into the cavity 338. The PTA catheter 390 is held in place by friction or other means.

In another embodiment, lips 333 are made from a relatively resilient material which allows for the flexing or opening of the lips 333 away from each other to allow the PTA catheter 390 to be inserted into the cavity 338, and once the flexing force is released, to allow the lips 333 to close in around the PTA catheter 390 to hold it in place.

The PTA catheter support structure 334 may incorporate a fluid delivery capability. This fluid delivery capability comprises one or more fluid passages in fluid communication with one or more fluid orifices. FIG. 3B shows a cross-sectional view of an embodiment of a support structure 334, which incorporates fluid orifices 340 in fluid communication with internal fluid passages 342 which allow cooling fluid to exit the support structure 334 near the PTA catheter 390 to provide for cooling of the treatment site. FIG. 3C shows a top view of an embodiment of a cooled support structure 336, which incorporates fluid orifices 341 along the length which allows cooling fluid to exit the support structure 336 to provide for cooling the treatment site.

Figure 4A:
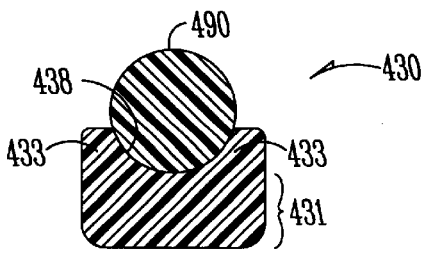
FIG. 4A is a cross-sectional view of one embodiment of a PTA catheter manipulation tool PTA catheter support structure with PTA catheter attached.

FIGS. 4A–F are views, illustrating generally, by way of example, but not by way of limitation, of embodiments of portions of the PTA catheter holding support structure. These embodiments may also incorporate fluid orifices to allow cooling of the treatment site. More in particular, FIG. 4A shows a cross-sectional view of a support structure 430. The PTA catheter support structure 430 comprises a concave channel having a base 431, spaced lips 433 extending from one side of the base 431 forming a cavity 438. In one embodiment, cavity 438 has a substantially circular cross section substantially conforming to and engaging a portion of the outer surface of the PTA catheter 490. The lips 433, extending from the base 431, partially surrounds the PTA catheter 490. PTA catheter 490 may be held in cavity 438 with an adhesive means.

Figure 4B:
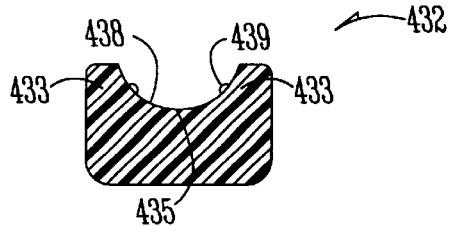
FIG. 4B is an end view of one embodiment of a PTA catheter manipulation tool PTA catheter support structure.

FIG. 4B shows a cross-sectional view of support structure 432 further comprising a gripping surface 435, within cavity 438, which is provided to engage and frictionally grip the PTA catheter. This gripping surface 435 may consist of a plurality of resilient ridges or bumps 439 provided to "grab hold" of the PTA catheter 490 when inserted into the cavity 438 of the support structure 430. In one embodiment, the support structure 432 is be made from a resilient material, such that lips 433 may be flexed or opened up away from each other to allow the insertion of the PTA catheter 490. Once inserted, the expansion force would be relieved and the bumps or ridges 439 would "grasp" the PTA catheter 490 while the lips 433 are closed around it.

Figure 4C:
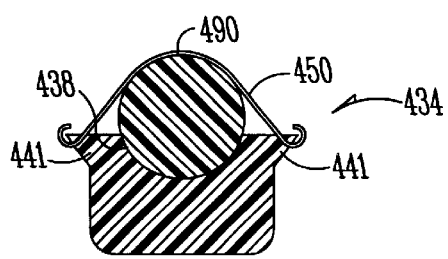
FIG. 4C is cross-sectional view of one embodiment of a PTA catheter manipulation tool PTA catheter support structure with suturable lips.
Figure 4D:
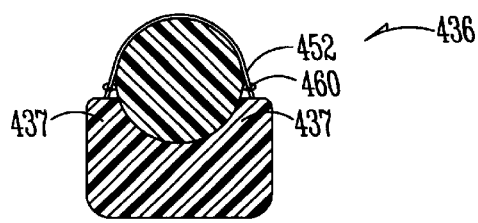
FIG. 4D is cross-sectional view of one embodiment of a PTA catheter manipulation tool PTA catheter support structure with hold-down members and loops.
Figure 4E:
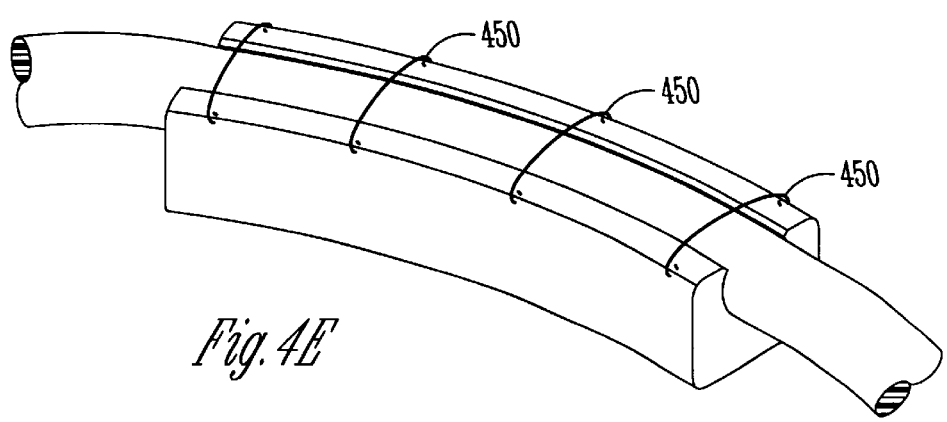
FIG. 4E is a perspective view of one embodiment of a PTA catheter manipulation tool PTA catheter support structure with hold-down members.
Figure 4F:
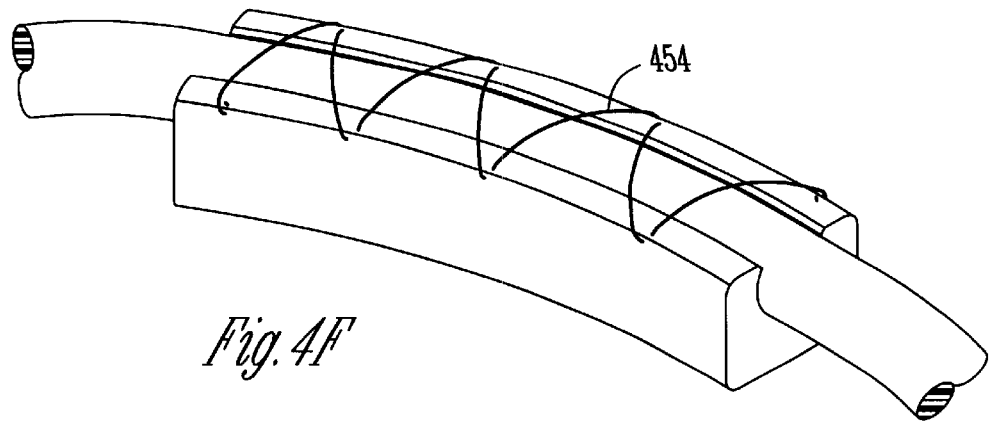
FIG. 4F is a perspective view of one embodiment of a PTA catheter manipulation tool PTA catheter support structure with hold-down member.

FIG. 4C is a cross-sectional view showing an embodiment of support structure 434 were the lip free ends 441 have the ability to be sutured into, such that suture 450 could be used to form hold-downs 450 that would hold the PTA catheter 490 onto the cavity 438. FIG. 4D is a cross-sectional view showing an embodiment of PTA catheter support structure 436 where the lips 437 incorporate suture loops 460 to facilitate the use of suture or other hold-down material to form hold-downs 452. FIG. 4E shows a top view of a portion of the support structure 434 with multiple single suture hold-downs 450. FIG. 4F shows a top view of a portion of the support structure 434 with a single running lace hold-down 454.

Figure 5A:
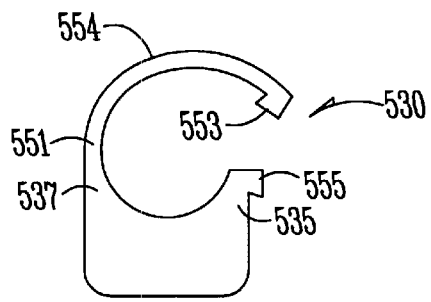
FIG. 5A is an end view of one embodiment of a PTA catheter manipulation tool PTA catheter support structure with hold-down latches.

FIGS. 5A–E are views, illustrating generally, by way of example, but not by way of limitation, of embodiments of portions of the PTA catheter holding support structure. These embodiments may also incorporate fluid orifices to allow cooling of the treatment site. FIG. 5A is an end view of an embodiment of PTA catheter support structure 530 having one or more clips 554. In this embodiment, the PTA catheter is attached to support structure 530 by clips 554. Clips 554 may incorporate a hinge means 551 attaching clips 554 to the other lip 537. Clips 554 may incorporate a latch means 553 which engages a catch means 555 on lip 535. Clips 554 may be made from a rigid material or a resilient material. Clips 554 and support structure 530 may be made as a single unit or as separate entities.

Figure 5B:
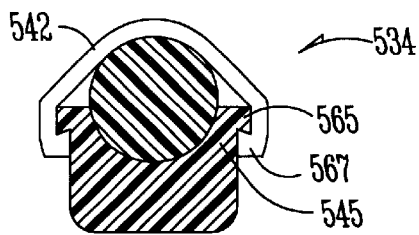
FIG. 5B is cross-sectional view of one embodiment of a PTA catheter manipulation tool PTA catheter support structure with hold-down clips.

FIG. 5B is a cross-sectional view of an embodiment of a PTA catheter support structure 534 that has one or more clips 542. In this embodiment, the PTA catheter is attached to support structure 534 by one or more clips 542 that are shaped to substantially conform to the shape of the PTA catheter. In one embodiment, one or more clips 542 is slidably inserted over the support structure 534. In another embodiment the one or more clips 542 are resilient or spring-like to allow flexing or opening up such that it can be placed over the PTA catheter 540 and support structure 534 and "clamped" around the support structure 534 holding the PTA catheter to the support structure 534. In one embodiment, lips 545 have an attachment means 565 that engages attachment means 567 on the one or more clips 542.

Figure 5C:
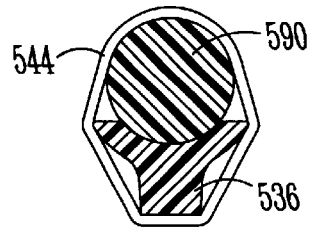
FIG. 5C is a cross-sectional view of one embodiment of a PTA catheter manipulation tool PTA catheter support structure with hold-down bands.

FIG. 5C is a cross-sectional view of another embodiment of the PTA catheter support structure 536. In this embodiment, PTA catheter 590 is held to the support structure 536 by use of one or more resilient bands 544.

Figure 6A:
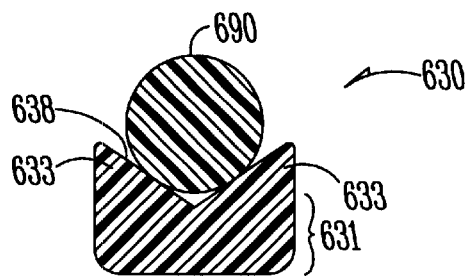
FIG. 6A is an end view of one embodiment of a PTA catheter manipulation tool PTA catheter support structure with attached PTA catheter.

FIGS. 6A–D are views, illustrating generally, by way of example, but not by way of limitation, of embodiments of portions of the PTA catheter holding support structure. These embodiments may also incorporate fluid orifices to allow cooling of the treatment site. FIG. 6A is a end view of an embodiment of the support structure 630 comprising a V cup having a base 631, spaced lips 633 extending from one side of the base 631 forming a cavity 638. Cavity 638 provides that the support structure 630 can accommodate various sizes (i.e., diameters) of PTA catheters 690. A portion of the PTA catheter 690, when placed within the cavity 638, is exposed above the lips 633. In one embodiment, the support structure 630 is made from a relatively rigid material. In one embodiment, the support structure 630 is malleable.

In one embodiment, the resilient force of the support structure 630 clamping down or squeezing is enough to hold the PTA catheter 690 in place. Hold-downs 490, 450, 452, 444, 554, 542, and 544 like the ones in FIGS. 4C, 4D, 4E, 4F, 5A, 5B and 5C respectively, may also be used as well as the use of bumps or ridges 439 as shown in FIG. 4B.

Figure 6B:
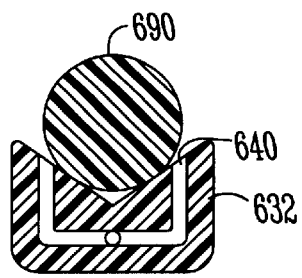
FIG. 6B is a cross-sectional view of one embodiment of a PTA catheter manipulation tool PTA catheter support structure with cooling capability and attached PTA catheter.
Figure 6C:
FIG. 6C is a cross-sectional view of one embodiment of a PTA catheter manipulation tool PTA catheter support structure with cooling capability.
Figure 6D:
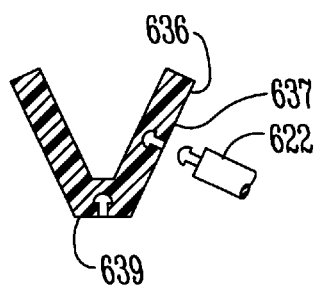
FIG. 6D is a cross-sectional view of one embodiment of a PTA catheter manipulation tool PTA catheter support structure with shaft attachment means.

FIG. 6B shows a cross-sectional view of another embodiment of the support structure 632 that incorporates one or more fluid orifices 640 and one or more fluid passages 632. FIG. 6C shows a cross-sectional view of another embodiment of the support structure 634 that incorporates fluid orifices 642. FIG. 6D shows a cross-sectional view of another embodiment of the support structure 636 that shows how removable or permanent attachment means of shaft 622 may be made; on the support structure side 637 and/or the support structure back 639.

Figure 7:
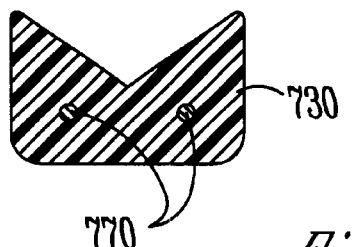
FIG. 7 is a cross-sectional view of one embodiment of a PTA catheter manipulation tool PTA catheter support structure.

FIG. 7 is a cross-sectional view, illustrating generally, by way of example, but not by way of limitation, of an embodiment of a portion of the PTA catheter holding support structure. This embodiment may also incorporate fluid orifices to allow cooling of the treatment site. FIG. 7 show a cross-sectional view of an embodiment of support structure 730 that has one or more malleable members 770. One or more malleable members 770, or substructure, are made from a material, and are sized and numbered, such that they impart a bend and stay property to the support structure 730 which would be made from a complementary material that allows the support structure 730 to be bendable. One or more malleable members 770 may be wires, rods, and flat sheet, among others. The one or more malleable members 770 are used in PTA catheter holding support structures of any shape; including those having a circular, V-shaped, and rectangular cross section.

Figure 8A:
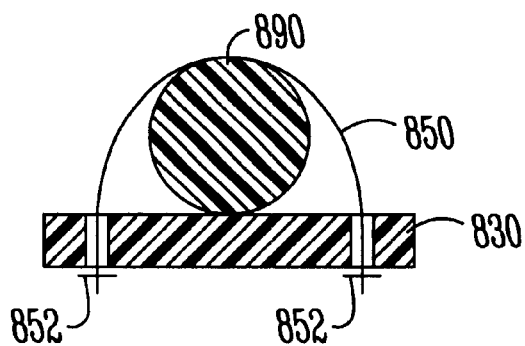
FIG. 8A is a cross-sectional view of one embodiment of a PTA catheter manipulation tool PTA catheter support structure with PTA catheter.
Figure 8B:
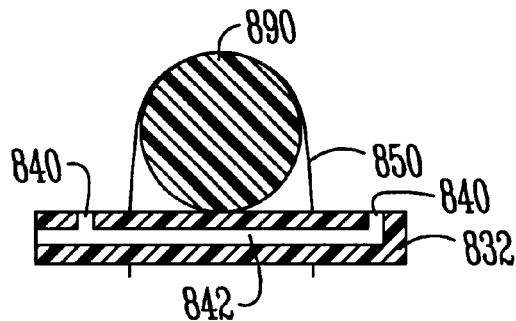
FIG. 8B is a cross-sectional view of one embodiment of a PTA catheter manipulation tool PTA catheter support structure with cooling capability and PTA catheter.

FIGS. 8A–D are views, illustrating generally, by way of example, but not by way of limitation, of embodiments of portions of the PTA catheter holding support structure. These embodiments may also incorporate fluid orifices to allow cooling of the treatment site. FIG. 8A is a cross-sectional view of an embodiment that has a flat-shaped support structure 830. The PTA catheter 890 is held onto the support structure 830 with the use of one or more hold-downs 850, such as suture, clips, bands, and the like. In one embodiment, the hold-downs 850 are integrally molded loops or rings that the PTA catheter is threaded through. In other embodiments, elastic loops, adhesive, and the like may be used to attach the PTA catheter 890 to the support structure 830. In one embodiment, the hold-downs 850 pass through the support structure 830 and are tied-off, or first passed through pledget 852 and then tied off. The pledget 852 helps to reinforce and resist suture-knot pull-out. FIG. 8B shows a cross-section of PTA catheter support structure 832 further comprising one or more fluid orifices 840 and one or more fluid passages 842.

Figure 8C:
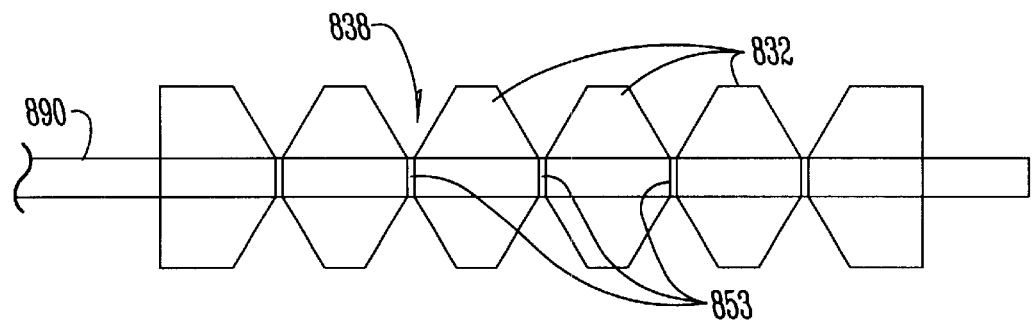
FIG. 8C is a top view of one embodiment of a PTA catheter manipulation tool PTA catheter support structure with PTA catheter.
Figure 8D:
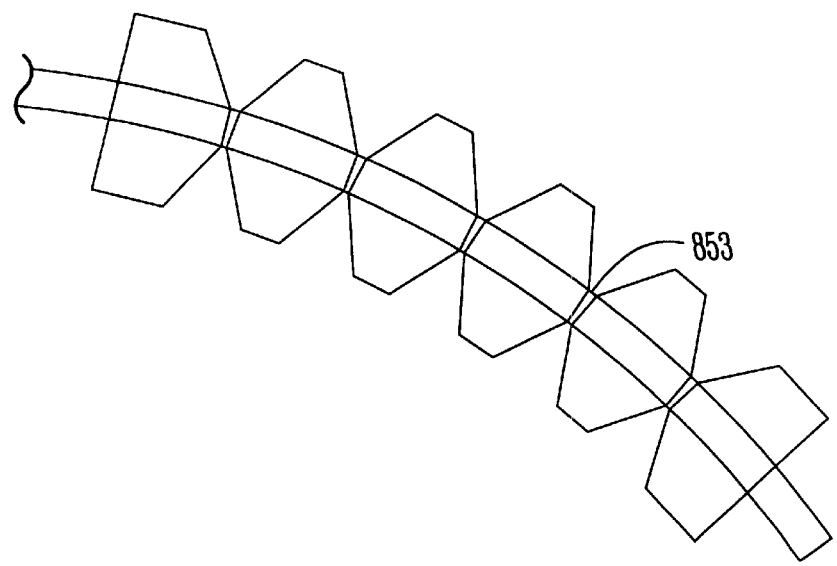
FIG. 8D is a top view of one embodiment of a PTA catheter manipulation tool PTA catheter support structure with PTA catheter.

FIGS. 8C and D are top views showing an embodiment of a flat-shaped support structure 832 having notch features 838 which facilitates the support structure 832 to be straight (FIG. 8C) or bent (FIG. 8D). PTA catheter 890 may be held onto the support structure 890 by the use of elastic bands, suture ties, and other hold-downs 853, wrapping the PTA catheter 890 and the support structure 832 in the notch feature 838. In one embodiment, the hold-downs 853 are one continuous piece wrapped around at least one notch feature 838 and the PTA catheter 890. In other embodiments, singular hold-downs 853 at each notch feature 838 and PTA catheter 890 location are used.

Figure 9:
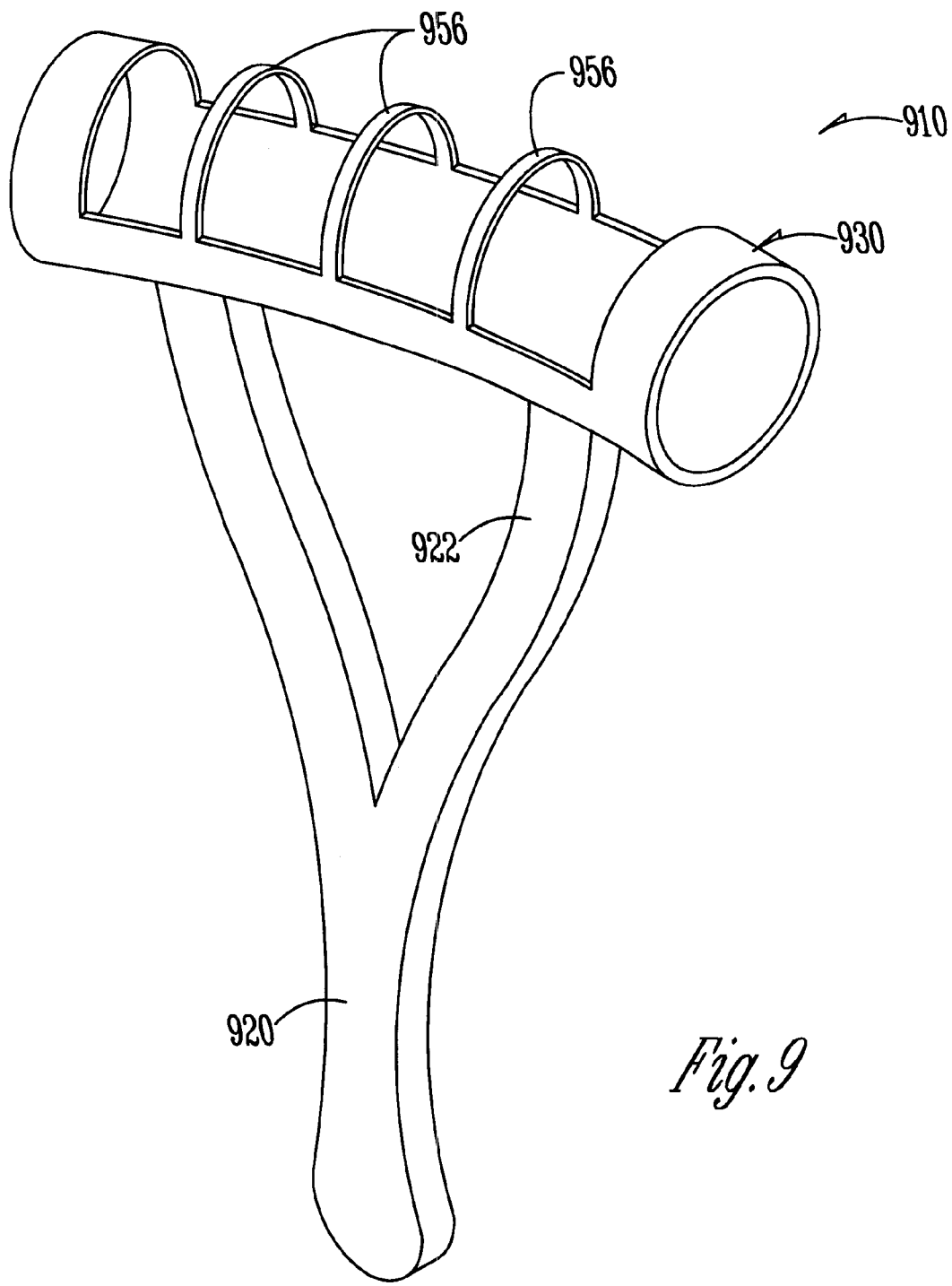
FIG. 9 is prospective view of one embodiment of a PTA catheter manipulation tool.

FIG. 9 is a perspective view of an embodiment of an PTA catheter manipulation tool 910 illustrating generally, by way of example, but not by way of limitation, one embodiment of an PTA catheter manipulation tool. More in particular, FIG. 9 shows an embodiment of the tool 910 consisting of a handle portion 920, two shafts 922 and a PTA catheter support structure 930. Support structure 930 further comprises loops 956 forming a substantially tubular shape through which a PTA catheter may be slidably inserted. A PTA catheter would be mounted to support structure 230 in such a way that the PTA catheter electrodes are exposed between the loops 956. In use, the user would hold the tool 910 by grasping the handle portion 920 and pressing the attached PTA catheter 990 against the treatment site.

Figure 10:
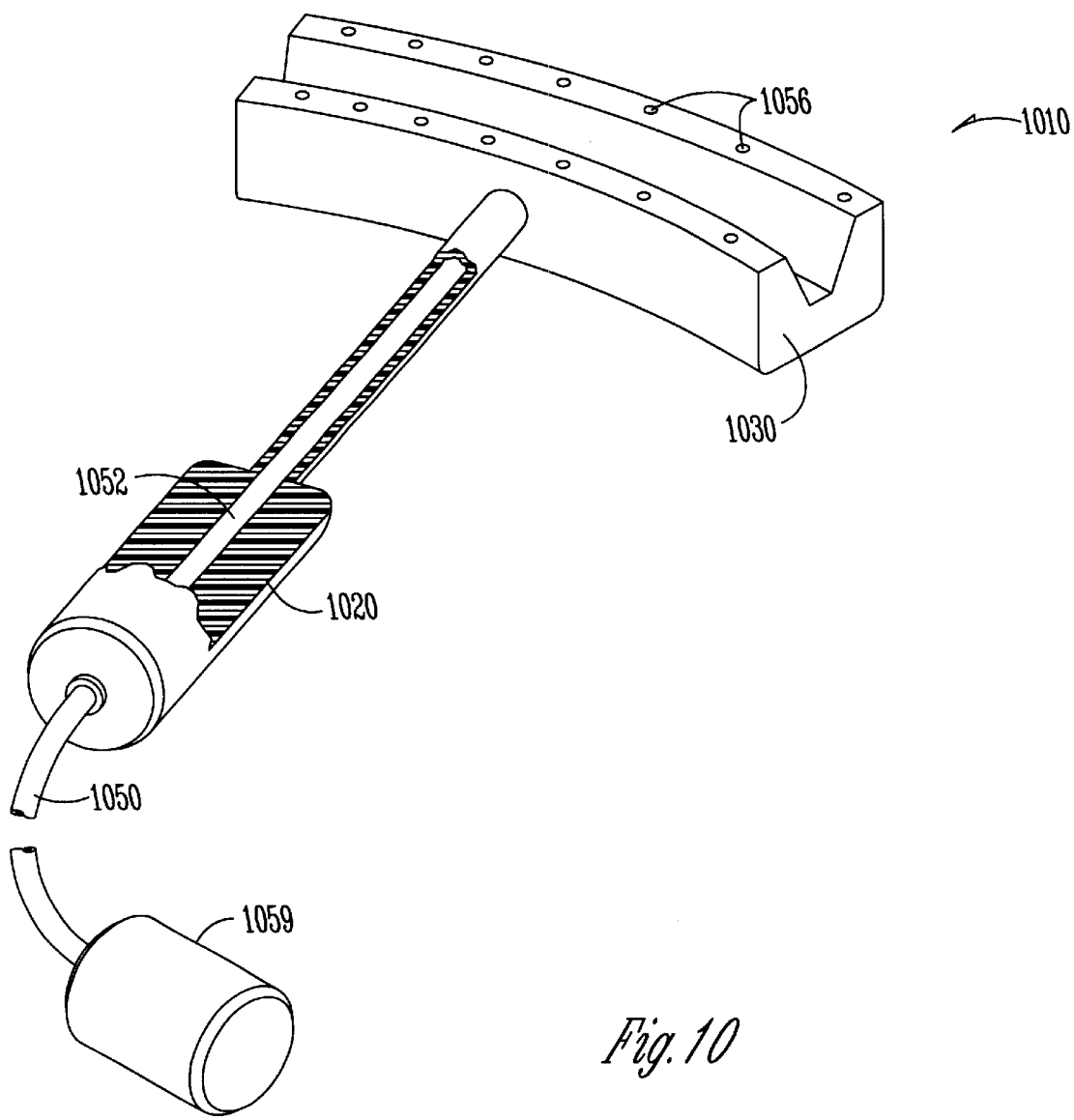
FIG. 10 is a partial cross-sectional perspective view of one embodiment of an ablation PTA catheter manipulation tool with cooling capability.

FIG. 10 is a top view, illustrating generally, by way of example, but not by way of limitation, of an embodiment of portions of the PTA catheter manipulation tool. In particular FIG. 10 shows an embodiment of a PTA catheter manipulation tool 1010 that has cooling capability. Fluid is supplied to the support structure 1030 from a fluid supply system 1059 via a fluid supply line 1050 that attaches to the handle portion 1020 that has an internal fluid channel 1052 in fluid communication with internal support structure fluid channels in fluid communication with a plurality of orifices 1056 which allow the cooling fluid to exit the orifices 1056 and drench the PTA catheter 1090 and the surrounding area.

Figure 11:
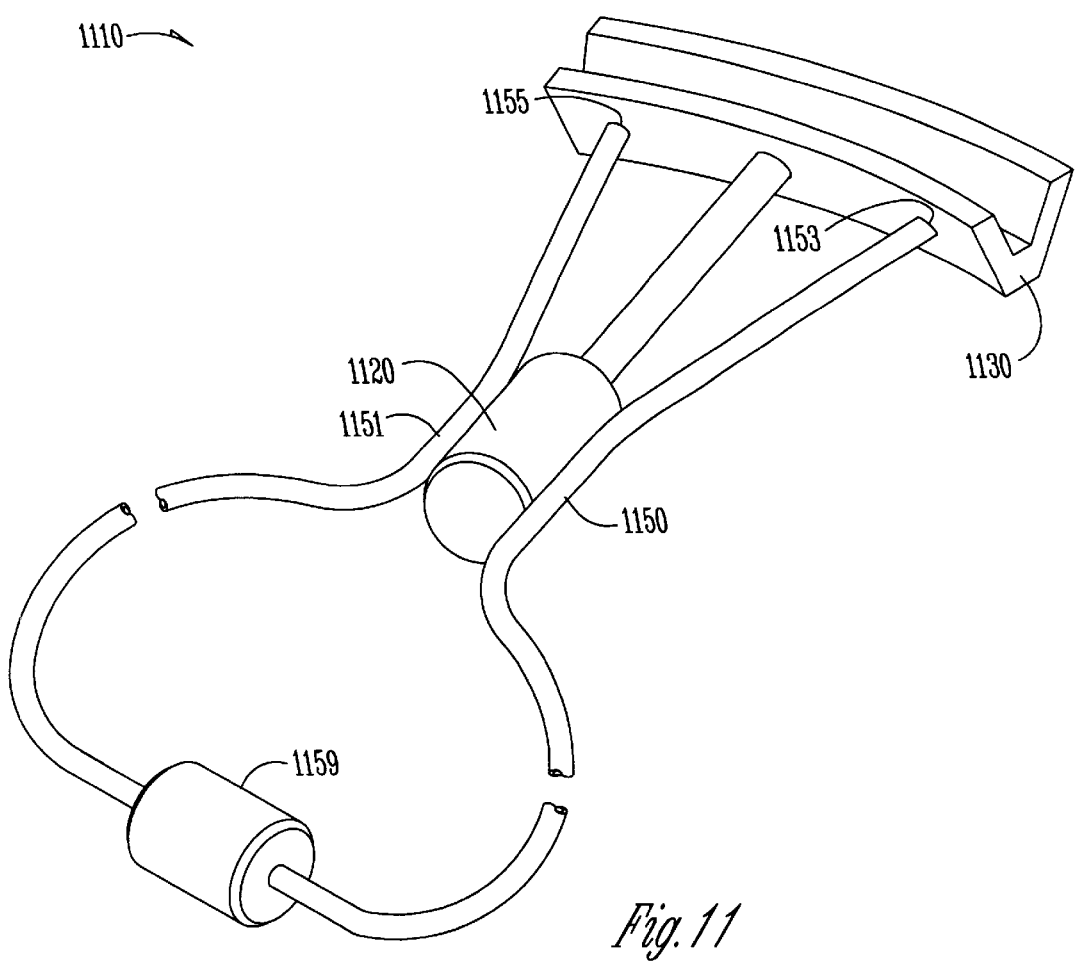
FIG. 11 is a perspective view of one embodiment of a PTA catheter manipulation tool with cooling capability.

FIG. 11 is a top view, illustrating generally, by way of example, but not by way of limitation, of an embodiment of portions of the PTA catheter manipulation tool. In particular FIG. 11 shows an embodiment of a PTA catheter manipulation tool 1110 that has cooling capability. The fluid is supplied to the support structure 1130 from a fluid supply system 1159 via a fluid supply line 1150 that may or may not attach to the handle portion 1120. The fluid supply line 1150 attaches to a connection means 1153 on the support structure 1130. The fluid line 1150 is in fluid communication with internal passages in the support structure 1130. The passages in the support structure 1130 are in fluid communication with a return fluid line 1151 that returns fluid to the supply system 1159 in a recirculating mainer. The fluid flowing through the passages cools the support structure 1130 during use.

Figure 12:
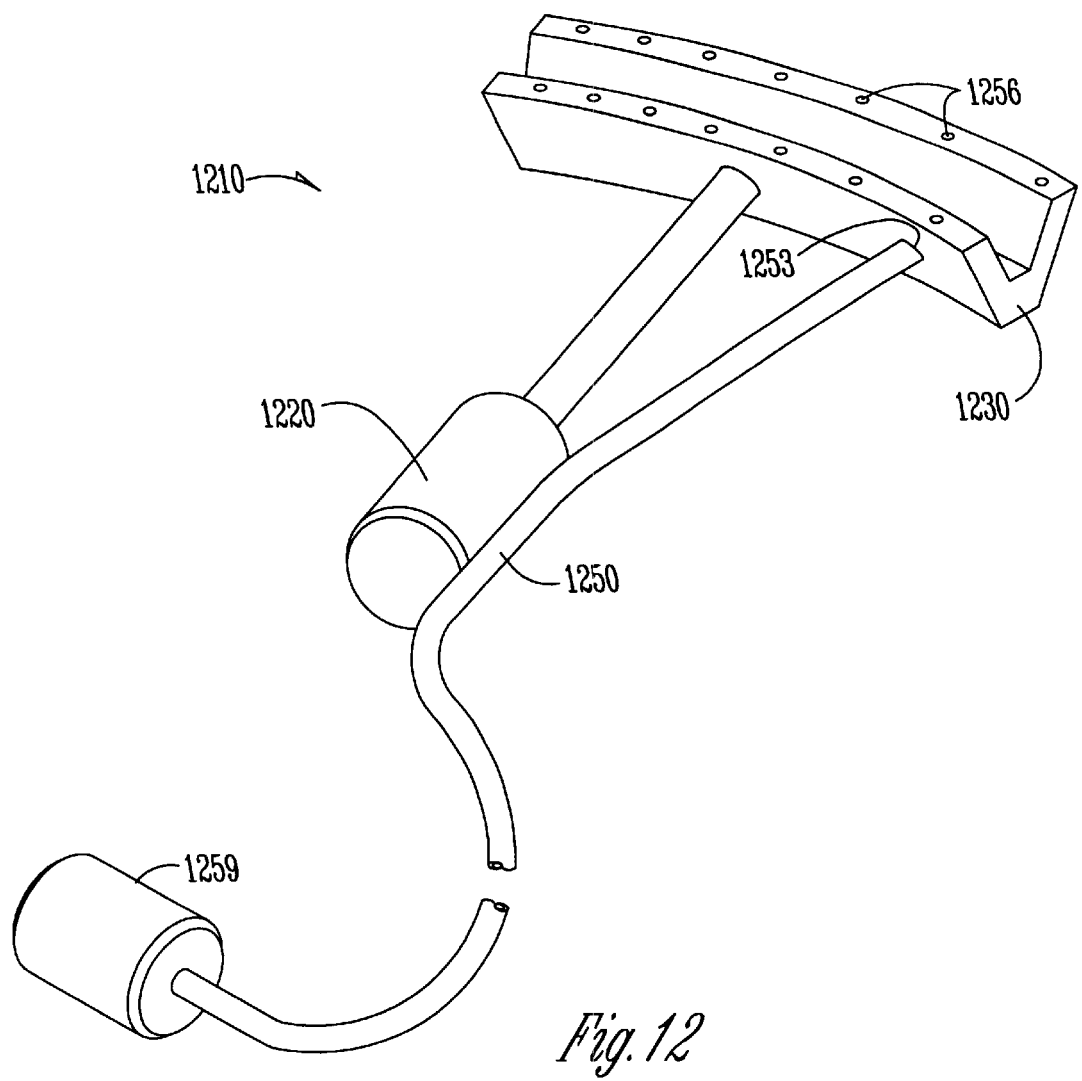
FIG. 12 is a perspective view of one embodiment of a PTA catheter manipulation tool with cooling capability.

FIG. 12 is a top view, illustrating generally, by way of example, but not by way of limitation, of an embodiment of portions of the PTA catheter manipulation tool. In particular FIG. 12 shows an embodiment of a PTA catheter manipulation tool 1210 that has cooling capability. The fluid is supplied to the support structure 1230 from a fluid supply system 1259 via a fluid supply line 1250 that may or may not attach to the handle portion 1220. The fluid supply line 1250 attaches to a connection means 1253 on the support structure 1230. The fluid line 1250 is in fluid communication with internal passages in the support structure 1230. The passages in the support structure 1230 are in fluid communication with orifices 1256 which allow the cooling fluid to exit the orifices 1256 and drench the PTA catheter and the surrounding area.

Figure 13A:
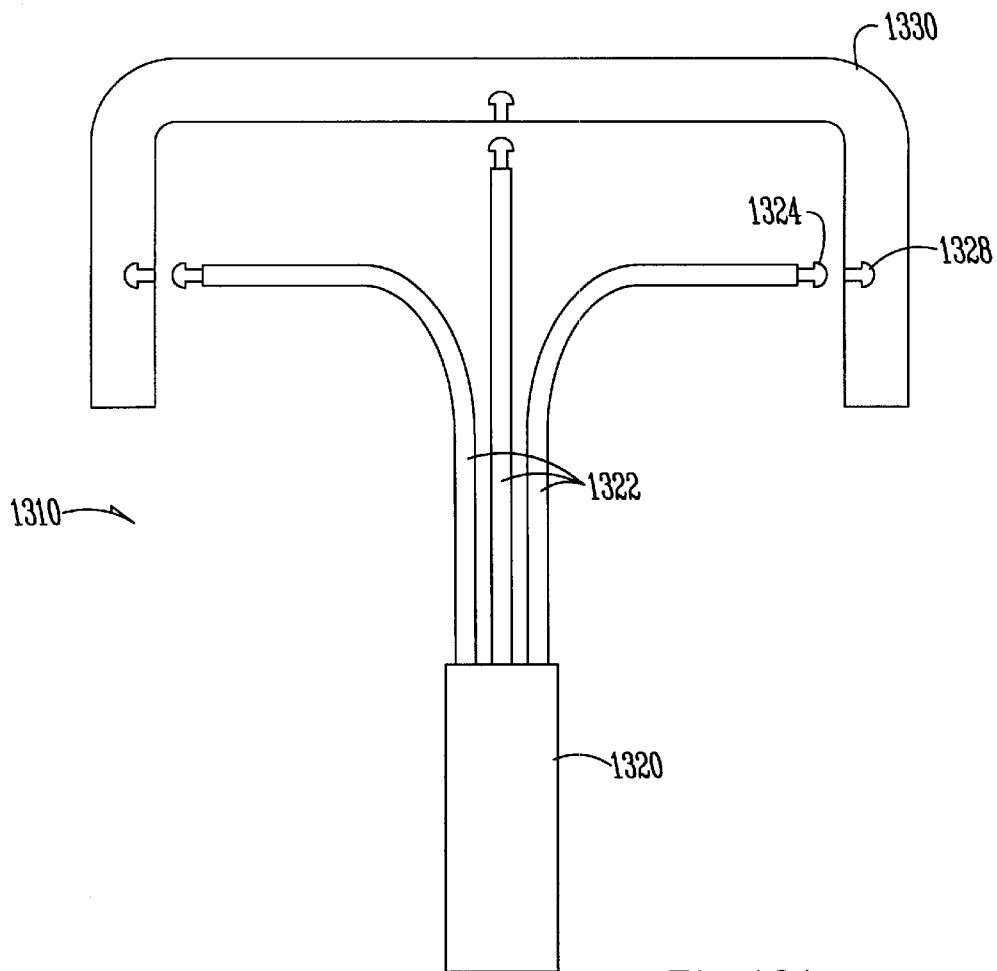
FIG. 13A is an exploded top view of one embodiment of a PTA catheter manipulation tool.
Figure 13B:
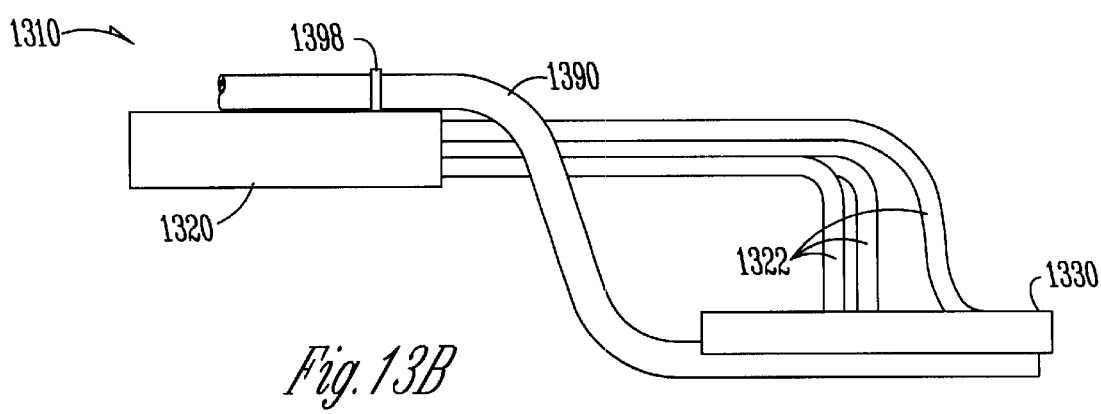
FIG. 13B is a side view of one embodiment of a PTA catheter manipulation tool with PTA catheter.

FIGS. 13A and 13B present a top and side view, respectively, illustrating generally, by way of example, but not by way of limitation, embodiments of the PTA catheter manipulation tool. In particular FIGS. 13A and B are exploded views showing an embodiment of the PTA catheter manipulation tool 1310 having multiple shafts 1322, handle portion 1320, and a PTA catheter holding support structure 1330. Attachment means 1324 on the shafts 1322 interrelate with attachment means 1328 on the support structure 1330 for a temporary or permanent connection. Attachment means 1324 and 1328 is a snap fitting, a screw fitting, a ratchet fitting, or any other means to temporarily or permanently connect the shafts 1322 to the support structure 1330. FIG. 13B shows a side view of the embodiment in FIG. 13A with the addition of PTA catheter 1390. PTA catheter 1390 may or may not be attached to the handle portion 1320 for support.

Figure 14:
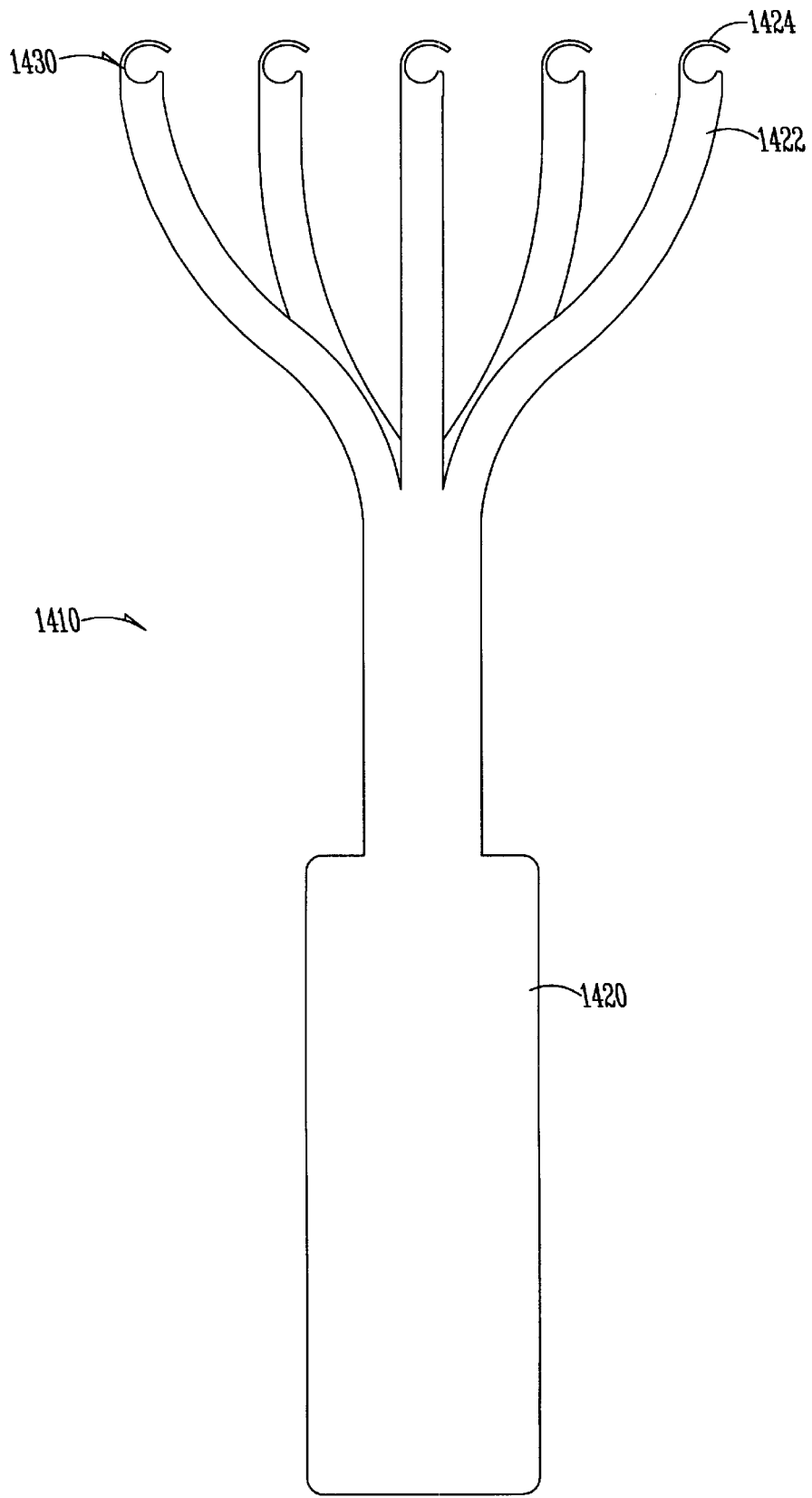
FIG. 14 is a top view of one embodiment of a PTA catheter manipulation tool.

FIG. 14 presents a top view illustrating generally, by way of example, but not by way of limitation, embodiments of the PTA catheter manipulation tool. In particular FIG. 14 shows an embodiment of the PTA catheter manipulation tool 1410 having a handle portion 1420, multiple independently bendable and adjustable shafts 1422, each shaft 1422 having a PTA catheter holding support structure 1430. The PTA catheter holding support structures 1430 may incorporate clips 1424, such as those shown in FIG. 5, for a temporary or permanent connection of a PTA catheter to the holding support structure 1430.

Operation and use of an embodiment of a PTA catheter manipulation tool can now be briefly described as follows. This example is not intended to be exclusive or limiting and the scope of the invention is provided by the attached claims and their equivalents. Let it be assumed that it is desired to introduce radio frequency energy into the wall forming a chamber of the heart to cause ablation of the myocardium. Also let it be assumed that the tool is introduced into the chamber of the heart in a human being in a conventional open heart procedure. By using operator experience and preference, the tool is bent and formed into a desired shape to allow convenient assess to the ablation site by the PTA catheter and to produce a lesion of the desired shape. The PTA catheter is attached to the PTA catheter holding support structure. The support structure is pressed against the tissue such that the PTA catheter is touching the tissue. Radio frequency is applied to the electrode which ablates the tissue. Fluid flows from the fluid supply system through the supply line and out the orifices in the support structure effectively cooling the surrounding tissue to minimize collateral tissue damage.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A percutaneous transluminal ablation (PTA) catheter manipulation tool, comprising:

a handle portion;

at least one shaft extending from the handle portion; and a PTA catheter support structure extending from an end of the at least one malleable shaft, the support structure further comprising a concave channel, said channel having a base and spaced lips each extending from one side of the base to form a cavity between the lips, each lip having a free end remote from the base, the cavity adapted to receive a PTA catheter, the cavity having a substantially circular cross section substantially conforming to and engaging a major portion of the outer surface of the PTA catheter when the PTA catheter fills that portion of the cavity, the lips extending from the base to partially overlap an attached PTA catheter, wherein said at least one shaft is malleable.

2. The tool according to claim 1 wherein said at least one shaft is detachable from said PTA catheter support structure.

3. The tool according to claim 1 wherein said at least one shaft is made from shape memory material, whereby the at least one shaft returns to the manufactured shape upon heating.

4. The tool according to claim 1 wherein said PTA catheter support structure is malleable.

5. A percutaneous transluminal ablation (PTA) catheter manipulation tool, comprising:

a handle portion; and a PTA catheter support structure extending from an end of said handle portion, the support structure comprising a concave channel, said concave channel having a base and spaced-apart resilient lips each extending from one side of the base to form a cavity between the lips, each lip having a free end remote from the base, the cavity adapted to receive a PTA catheter, the cavity having a substantially circular cross section substantially conforming to and engaging a major portion of the outer surface of the PTA catheter when the PTA catheter fills that portion of the cavity, the lips extending from the base to partially overlap an attached PTA catheter.

6. A percutaneous transluminal ablation (PTA) catheter manipulation tool, comprising:

a handle portion;

a PTA catheter support structure extending from an end of said handle portion, the support structure further comprising a concave channel, said concave channel having a base and spaced lips each extending from one side of the base to form a cavity between the lips, each lip having a free end remote from the base, the cavity adapted to receive a PTA catheter, the cavity having a substantially circular cross section substantially conforming to and engaging a major portion of the outer surface of the PTA catheter when the PTA catheter fills that portion of the cavity, the lips extending from the base to partially overlap an attached PTA catheter; and a fluid delivery means comprising the handle portion having a fluid connector means for a fluid supply means, and at least one internal fluid passage in fluid communication with the connector means, the PTA catheter support structure having at least one internal fluid passage in fluid communiation with said at least one handle portion internal fluid passage, and at least one fluid orifice in fluid communication with said at least one support structure internal fluid passage, the fluid delivery means adapted to accept fluid into the connector means and discharge fluid out the at least one orifice adapted to bathe the PTA catheter and surrounding area with fluid.

7. A percutaneous transluminal ablation (PTA) catheter manipulation tool, comprising:

a handle portion; and a PTA catheter support structure extending from an end of said handle portion, the support structure further comprising a concave channel, said concave channel having a base and spaced lips each extending from one side of the base to form a cavity between the lips, each lip having a free end remote from the base, the cavity having a substantially circular cross section adapted to substantially conform to and engage a portion of the outer surface of the PTA catheter when the PTA catheter fills that portion of the cavity, the cavity having a gripping surface.

8. The tool according to claim 7 wherein the gripping surface further comprises at least one resilient ridge, whereby the at least one ridge aids in retaining the PTA catheter within the cavity.

9. The tool according to claim 7 wherein the gripping surface further comprises at least one resilient bump, whereby the at least one bump aids in retaining the PTA catheter within the cavity.

10. A percutaneous transluminal ablation (PTA) catheter manipulation tool, comprising:

a handle portion; and a PTA catheter support structure extending from an end of said handle portion, the support structure further comprising a concave channel, said concave channel having a base and spaced lips each extending from one side of the base to form a cavity between the lips, each lip having a free end remote from the base, the cavity having a substantially circular cross section adapted to substantially conform to and engage a portion of the outer surface of the PTA catheter when the PTA catheter fills that portion of the cavity, and further comprising a hold-down means adapted to retain the PTA catheter within the cavity.

11. The tool according to claim 10 wherein the hold-down means comprises at least one elastic band, the at least one band sized to be stretched over the PTA catheter and support structure, whereby the at least one band aids in retaining the PTA catheter within the cavity.

12. The tool according to claim 10 wherein the hold-down means comprises at least one clip substantially conforming to and engaging a major portion of the outer surface of the PTA catheter and PTA catheter support structure, whereby the at least one clip aids in retaining the PTA catheter within the cavity.

13. The tool according to claim 10 wherein the lips are capable of being sutured and the hold-down means comprises suture, whereby the suture may be threaded through the lips and over the PTA catheter forming a lace, thereby retaining the PTA catheter within the cavity.

14. The tool according to claim 10 wherein the hold-down means comprises at least one latch, said at least one latch hingeably connected to the first lip and the second lip having a corresponding catch means, such that the latch bridges the two lips thereby retaining the PTA catheter within the cavity.

15. A perculaneous transluminal ablation (PTA) catheter manipulation tool having a cavity that can accommodate PTA catheters of different diameters, comprising:
 a handle portion; and
 a PTA catheter support structure extending from an end of said handle portion,
 the support structure further comprising a concave channel, said concave channel having a base and spaced lips each extending from one side of the base to form a cavity between the lips, each lip having a free end remote from the base, wherein the cavity has a substantially V-shaped cross section, the cavity adapted to cradle the PTA catheter, the PTA catheter support structure further comprising a PTA catheter hold-down means, said hold-down means securing the PTA catheter in the cavity, the cavity having a gripping surface.

16. The tool according to claim 15 further comprising at least one shaft between the handle portion and the PTA catheter support structure.

17. The tool according to claim 16 wherein said at least one shaft is malleable.

18. The tool according to claim 17 wherein said at least one shaft is made from shape memory material, whereby the at least one shaft returns to the manufactured shape upon heating.

19. The tool according to claim 16 wherein said at least one shaft is detachable from said PTA catheter support structure.

20. The tool according to claim 15 wherein said PTA catheter support structure is malleable.

21. The tool according to claim 15 having fluid delivery means comprising:
 the handle portion including a fluid connector means for a fluid supply means, and at least one internal fluid passage in fluid communication with the connector means, and
 the PTA catheter support structure including at least one internal fluid passage in fluid communcation with said at least one handle portion internal fluid passage, and at least one fluid orifice in fluid communcation with at leat one support structure internal fluid passage, the fluid delivery means adapted to accept fluid into the connector means and discharge fluid out the at least one orifice adapted to bathe the PTA catheter and surrounding area with fluid.

22. The tool according to claim 15 wherein the hold-down means comprises at least one resilient ridge on the gripping surface, whereby the at least one ridge aids in retaining the PTA catheter within the cavity.

23. The tool according to claim 15 wherein the hold-down means comprises at least one resilient bump on the gripping surface, whereby the at least one bump aids in retaining the PTA catheter within the cavity.

24. The tool according to claim 15 wherein the hold-down means comprises at least one elastic band, the at least one band sized to be stretched over the PTA catheter support structure and attached PTA catheter, whereby the at least one band aids in retaining the PTA catheter within the cavity.

25. The tool according to claim 15 wherein the hold-down means comprises at least one spring clip substantially conformiing to and engaging a major portion of the outer surface of the PTA catheter and PTA catheter support structure assembly.

26. The tool according to claim 15 wherein the lips are capable of being sutured and the hold-down means comprises suture, whereby the suture may be threaded through the lips and over the PTA catheter forming a lace, thereby retaining the PTA catheter within the cavity.

27. The tool according to claim 15 wherein the hold-down means further comprises at least one latch, said at least one latch hingeably connected to a first lip and the other lip having a corresponding catch means, such that the latch bridges the two lips thereby retaining the PTA catheter within the cavity.

28. A percutaneous transluminal ablation catheter manipulation tool, comprising:
 a handle portion; and
 a PTA catheter support structure extending from an end of said handle portion,
 the support structure further comprising a substantially planer platform, and a PTA catheter hold-down means, said hold-down means securing the PTA catheter in the platform.

29. The tool according to claim 28 further comprising at least one shaft between the handle portion and the PTA catheter support structure.

30. The tool according to claim 29 wherein said at least one shaft is malleable.

31. The tool according to claim 30 wherein said at least one shaft is made from shape memory material, whereby the at least one shaft returns to the manufactured shape upon heating.

32. The tool according to claim 29 wherein said at least one shaft is detachable from said PTA catheter support structure.

33. The tool according to claim 28 wherein the support structure is pivotally mounted to the handle portion.

34. The tool according to claim 28 wherein said PTA catheter support structure is malleable.

35. The tool according to claim 34 wherein said PTA catheter support structure is substantially rectangular, the long edges having one or more notches, whereby the one or more notches open or close to facilitate bending.

36. The tool according to claim 28 having fluid delivery means further comprising:
 the handle portion including a fluid connector means for a fluid supply means, and at least one internal fluid passage in fluid communication with the connector means,
 the PTA catheter support structure including at least one internal fluid passage in fluid communication with said at least one handle portion internal fluid passage, and at least one fluid orifice in fluid communication with said at least one support structure internal fluid passage, the fluid delivery means adapted to accept fluid into the connector means and discharge fluid out the as least one orifice adapted to bathe the PTA catheter and surrounding area with fluid.

37. The tool according to claim 28 wherein the hold-down means comprises at least one elastic band, the at least one band sized to be stretched over the PTA catheter support structure and attached, whereby the at least one band aids in retaining the PTA catheter within the cavity.

38. The tool according to claim 28 wherein the hold-down means comprises at least one spring clip substantially conforming to and engaging a major portion of the outer surface of the PTA catheter and PTA catheter support structure assembly, whereby the at least one spring clip aids in retaining the PTA catheter within the cavity.

39. The tool according to claim 28 wherein the platform is capable of being sutured and the hold-down means comprises suture, whereby the suture may be threaded through the platform and over the attached PTA catheter forming a lace, whereby retaining the PTA catheter within the cavity.

40. The tool according to claim 28 wherein the hold-down means further comprises at least one latch, said at least one latch hingeably connected to the first platform edge and the opposite platform edge having a corresponding catch means, such that the latch bridges the two edges whereby retaining the attached PTA catheter on the platform.

41. A method for ablating tissue non-transluminally using a percutaneous transluminal ablation (PTA) catheter comprising:

exposing target tissue of the patient's heart using conventional open heart procedures;

bending and forming a PTA catheter manipulation tool, having a PTA catheter holding support structure, into a desired shape, thereby allowing convenient access to the ablation site by an attached PTA catheter and to produce a lesion of the desired shape;

attaching a PTA catheter to the PTA catheter holding support structure;

pressing the PTA catheter support structure against the tissue such that the PTA catheter is in contact with the tissue;

initiating fluid flow from a fluid supply system, thereby the fluid flows through the supply line and out orifices in the PTA catheter support structure cooling the surrounding tissue minimizing collateral tissue damage;

applying energy to the PTA catheter thereby the PTA catheter electrodes ablate the tissue;

terminating the supply of energy to the PTA catheter after sufficient time to produce the desired lesion;

terminating the flow of fluid from the fluid supply system; and withdrawing the PTA catheter manipulation tool from the tissue site.

\* \* \* \* \*

UNITED STATES PATENT AND TRADEMARK OFFICE
CERTIFICATE OF CORRECTION

PATENT NO.   : 6,364,878 B1
DATED        : April 2, 2002
INVENTOR(S)  : Hall

It is certified that error appears in the above-identified patent and that said Letters Patent is hereby corrected as shown below:

Column 11,
Line 26, after "said" insert -- concave --.
Line 50, after "structure" insert -- further --.

Column 13,
Line 19, delete "perculaneous" and insert -- percutaneous --, therefor.
Line 58, delete "leat" and insert -- least --, therefor.
Line 58, after "with" insert -- said --, therefor.

Column 14,
Line 11, delete "conformiing" and insert -- conforming --, therefor.

Column 15,
Line 1, delete "as" and insert -- at --, therefor.

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,364,878 B1
DATED : April 2, 2002
INVENTOR(S) : Hall

It is certified that error appears in the above-identified patent and that said Letters Patent is hereby corrected as shown below:

<u>Title page,</u>
Item [56], References Cited, U.S. PATENT DOCUMENTS,
After "KenKnight et al." insert -- 607/132 --.
After "12/1995 Kordis et al." insert -- 607/122 --.
After "Garrison et al." insert -- 600/201 --.
After "Webster" insert -- 128/642 --.
After "6/1997 Kordis et al." insert -- 128/642 --.
After "van Muiden et al." insert -- 604/9 --.
After "Imran et al." insert -- 606/41 --.
After "Edwards et al." insert -- 604/22 --.
After "Krueger et al." insert -- 632/2 --.
After "Wallner et al." insert -- 623/2 --.
Delete "Wallnner" and insert -- Wallner --, therefor.
After "Fleischman et al." insert -- 606/47 --.
After "Lundquist et al." insert -- 604/22 --.
OTHER PUBLICATIONS, delete "vol. 83" and insert -- Volume 83 --, therefor.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,364,878 B1
DATED : April 2, 2002
INVENTOR(S) : Hall

It is certified that error appears in the above-identified patent and that said Letters Patent is hereby corrected as shown below:

Title page,
Item [56], References Cited, U.S PATENT DOCUMENTS, insert
-- 5,242,430 A   9/1993   Arenas et al. ................ 604/280- --.
Insert
-- FOREIGN PATENT DOCUMENTS
CA     2234444     11/1998 .......... A61M/25/01
FR     2650957     02/1991 ........ A61M/25/02
WO    96/01592    01/1996 ........ A61B/17/34 --.

Signed and Sealed this

Fifteenth Day of March, 2005

JON W. DUDAS
*Director of the United States Patent and Trademark Office*